(12) United States Patent
DeSilva et al.

(10) Patent No.: US 10,286,134 B2
(45) Date of Patent: May 14, 2019

(54) VENTRICULAR ASSIST DEVICE

(71) Applicants: Peter DeSilva, Rancho Santa Margarita, CA (US); Steve Smith, Trabuco Canyon, CA (US)

(72) Inventors: Peter DeSilva, Rancho Santa Margarita, CA (US); Steve Smith, Trabuco Canyon, CA (US)

( * ) Notice: Subject to any disclaimer, the term of this patent is extended or adjusted under 35 U.S.C. 154(b) by 0 days.

(21) Appl. No.: 15/405,210

(22) Filed: Jan. 12, 2017

(65) Prior Publication Data

US 2018/0193542 A1 Jul. 12, 2018

(51) Int. Cl.
*A61M 1/10* (2006.01)
*A61M 1/12* (2006.01)

(52) U.S. Cl.
CPC ............ *A61M 1/122* (2014.02); *A61M 1/101* (2013.01); *A61M 1/1008* (2014.02); *A61M 1/1012* (2014.02); *A61M 1/1017* (2014.02); *A61M 1/1084* (2014.02); *A61M 1/127* (2013.01); *A61M 1/1031* (2014.02)

(58) Field of Classification Search
CPC .. A61M 1/122; A61M 1/1008; A61M 1/1036; A61M 1/1017

USPC .......................................................... 600/16
See application file for complete search history.

(56) References Cited

U.S. PATENT DOCUMENTS

| | | | |
|---|---|---|---|
| 2005/0085684 A1* | 4/2005 | Rakhorst | A61M 1/107 600/16 |
| 2006/0122456 A1* | 6/2006 | LaRose | A61M 1/1017 600/16 |

* cited by examiner

*Primary Examiner* — Amanda K Hulbert
*Assistant Examiner* — Philip C Edwards
(74) *Attorney, Agent, or Firm* — Roy A. Ekstrand

(57) ABSTRACT

A ventricular assist device for use in a human recipient includes a housing within which a series pair of turbine pump segments are operative. The series pair of turbine pump segments provides a redundancy in turn enhances the safety factor provided by the ventricular assist device. A controller is powered by a rechargeable battery and is operative to apply appropriate drive signals to the motor drives of the turbine pump segments. The battery may be implanted along with the controller to avoid the need for any external connections to the ventricular assist device. An inductively coupled batter charger for use outside the recipient's body is positioned proximate the battery charger to provide inductively coupled charging for use in driving the ventricular assist device.

13 Claims, 13 Drawing Sheets

VENTRICULAR ASSIST DEVICE

FIELD OF THE INVENTION

This invention relates generally to apparatus for sustaining and continuing life for patients having failing or failed hearts and particularly to artificial devices, known generally in the art as "Ventricular Assist Devices" (VADs), including ventricular assist devices such as "Left Ventricle Assist Devices" (LVADs) used to supplement the performance of weak or failing hearts. This invention also further relates to issued patent U.S. Pat. No. 9,314,559, issued to Steve Smith and Peter DeSilva, entitled FOUR CHAMBER REDUNDANT-IMPELLER ARTIFICIAL HEART, the disclosure of which is hereby incorporated herein by reference.

BACKGROUND OF THE INVENTION

For many years, practitioners in the medical treatment and medical device arts have endeavored to provide artificial heart devices constructed to replace a failed or failing heart within a recipient. The most basic long term need is the creation of a replacement pumping device which is capable of performing the basic blood pumping and circulation functions of the natural heart.

Early attempts to provide a sustainable heart replacement were severely limited by the available technologies and the state of the art at that time. Devices proved to be generally too large and unwieldy and, for the most part, impractical. With the continuing advances in the related technologies and creative arts, heart replacement devices became smaller, more reliable and, in some instances, at least partially implantable within the recipient. Such "implantable" devices have generally remained hybrid devices in that the actual pump may be implanted within the recipient while additional support apparatus remains external to the patient and remains connected to the implanted device by a plurality of connecting wires and hoses.

One of the more recent attempts to provide a reliable and practical artificial heart device which embodies great promise, is shown in the above referenced and incorporated U.S. Pat. No. 9,314,559 which sets forth an artificial heart for use in a human recipient that includes a housing within which a quartet of turbine pump segments are operative. The quartet of turbine pump segments provides a redundancy which in turn enhances the safety factor provided by the artificial heart. A controller is powered by a rechargeable battery and is operative to apply appropriate drive signals to the motor drives of the turbine pump segments. The battery may be implanted along with the controller to avoid the need for any external connections to the artificial heart. An inductively coupled battery charger for use outside the recipient's body is positioned proximate the battery charger to provide inductively coupled charging for use in driving the artificial heart.

In a field of endeavor closely related to the attempts to provide a practical and reliable implantable artificial heart, practitioners have also been addressing the need for a ventricular assist device. Such ventricular assist devices (VADs) supplement the performance of a weakened heart without fully replacing it. Ventricular assist devices provide an implantable mechanical pump that helps blood flow from the lower chambers of a weakened heart, the ventricles, to other parts of the body or other parts of the heart itself. One of the most prevalent uses of such ventricular assist devices, known as LVAD, is implanted in the patient's chest cavity and is used to pump blood from the lower portion of the left ventricle to the heart aorta.

A successful ventricular assist device must, above all, be long lasting and reliable. The dire consequences to the device recipient brought about by device failure make this requirement all too apparent. In addition, however, the device must be small enough to be implantable within the recipient's chest and efficient enough to maintain adequate blood circulation to sustain normal life functions. The device must avoid undue stress upon the recipient's circulatory and pulmonary systems. The device must also be capable of adjusting to and compensating for different recipient activity levels and stress. Additional requirements such as avoidance of blood cell damage by the pumping apparatus and the prevention of blood clot forming stagnation regions make further demands upon ventricular assist devices.

While practitioners in the medical treatment and medical device arts have created a virtually endless number of proposed artificial ventricular assist devices, there remains nonetheless a continuing unresolved need in the art for an improved, implantable, reliable and effective artificial ventricular assist device which meets the stringent, unforgiving and vital requirements and challenges posed by a truly fully functioning completely implantable ventricular assist device.

SUMMARY OF THE INVENTION

Accordingly, it is a general object of the present invention to provide an artificial ventricular assist device which is reliable, implantable and effective. It is a more particular object of the present invention to provide an improved ventricular assist device which avoids the need for external component apparatus and which signals events or anomalies within the system while shifting to backup remedial life sustaining operation.

In accordance with the present invention, there is provided a ventricular assist device comprising: a housing having an input connector and an output connector, a first turbine pump operative to flow blood from the input connector to the output; a second turbine pump operative to flow blood from the input connector to the output connector;

The present invention improves the art by providing a dual stage redundant impeller ventricular assist device. Within the housing a pair of electrically-driven impeller drive motors facilitate the pumping of blood from one portion of the circulatory system to another portion of the circulatory system, such as from the lower left ventricle to the aorta. The use of dual pump drives for the pump turbines is configured to provide complete pump redundancy should a pump fail. In such case, the remaining operative motor/pump drives the turbines coupled thereto with sufficient capability and circulation to maintain life in the recipient until remedial intervention may be performed. The output from the pump supports a sensor coupled to a dual microprocessor drive controller. Each microprocessor drive controller is operatively coupled to both of the redundant pump drive motors. Sensors are also provided to monitor the operation of each pump system. A pair of battery modules each including an inductively coupled charging device are implanted within the patient abdomen and operatively coupled to the processor controller and the drive motors. A pair of inductive battery charging modules are supported upon an abdominal belt and coupled to a source of operative electrical power. Battery charging is accomplished by inductive coupling through the body tissue between the external charging modules and the implanted battery and charger apparatus. The dual redundant micro controller is also implanted within the recipient's body.

From another perspective, the present invention provides a ventricular assist device comprising: a housing having an input, an output, a first turbine pump operative to flow blood from the input to the output; a second turbine pump operative to flow blood from the input to the output. In a preferred fabrication of the present invention ventricular assist device, the first and second turbine pumps are arranged in series pairs within the blood flow. The turbine pumps are supported within a housing defining a straight-through blood flow path, supporting the series pair of turbine pumps.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS OF THE INVENTION

Figure 1:
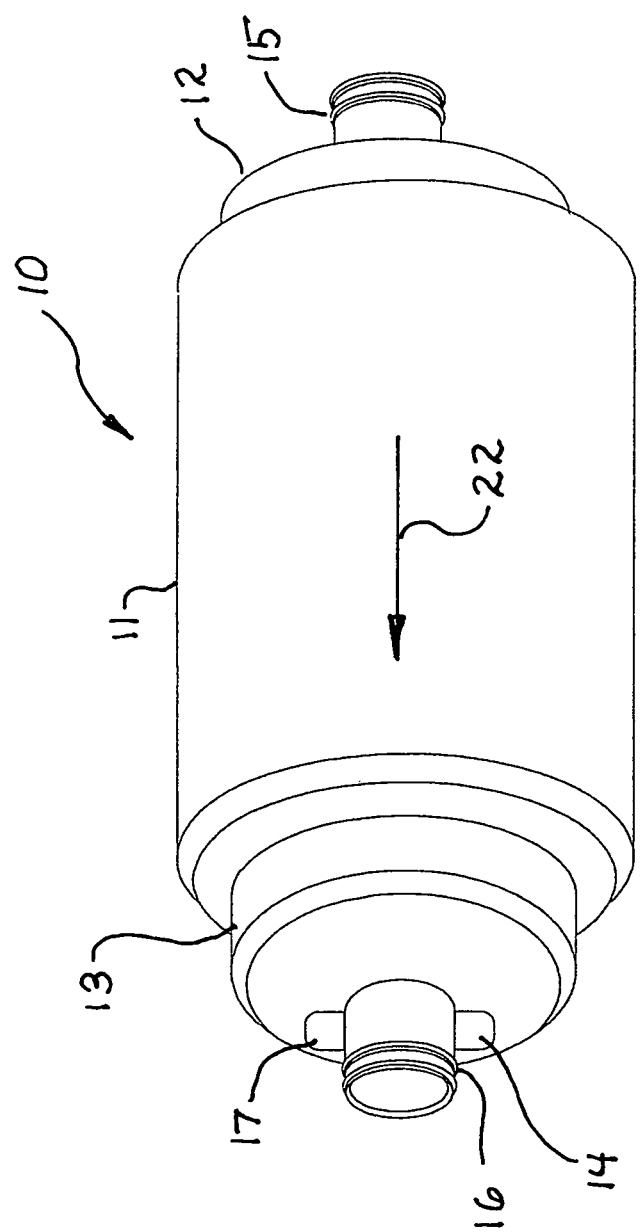
FIG. 1 sets forth a perspective view of a ventricular assist device constructed in accordance with the present invention.

FIG. 1 sets forth a perspective view of a ventricular assist device constructed in accordance with the present invention and generally referenced by numeral 10 ventricular assist device 10 includes a generally cylindrical housing 11 supporting a pair of end caps 12 and 13. End 12 further supports and input connector 15 while end cap 13 further supports an output connector 16. A pair of output flow "pressure" sensors 14 and 17 are supported upon output connector 16. In its preferred fabrication, housing 11 and end caps 12 and 13 together with connectors 15 and 16 are formed of a medically approved suitable molded plastic material or the like. By operation set forth below in greater detail, ventricular assist device 10 is operative to pump a flow of blood coupled to input connector 15 through housing 11 to exit at output connector 16. As is better seen below in FIG. 2, conventional hose connectors 20 and 21 are coupled to input connector 15 and output connector 16 respectively to provide blood flow which is pumped through ventricular assist device 10. It will be apparent to those skilled in the art that the small compact generally cylindrical shape of ventricular assist device 10 is well adapted to being implanted within a recipient's chest cavity in the manner shown in FIG. 4.

Figure 2:
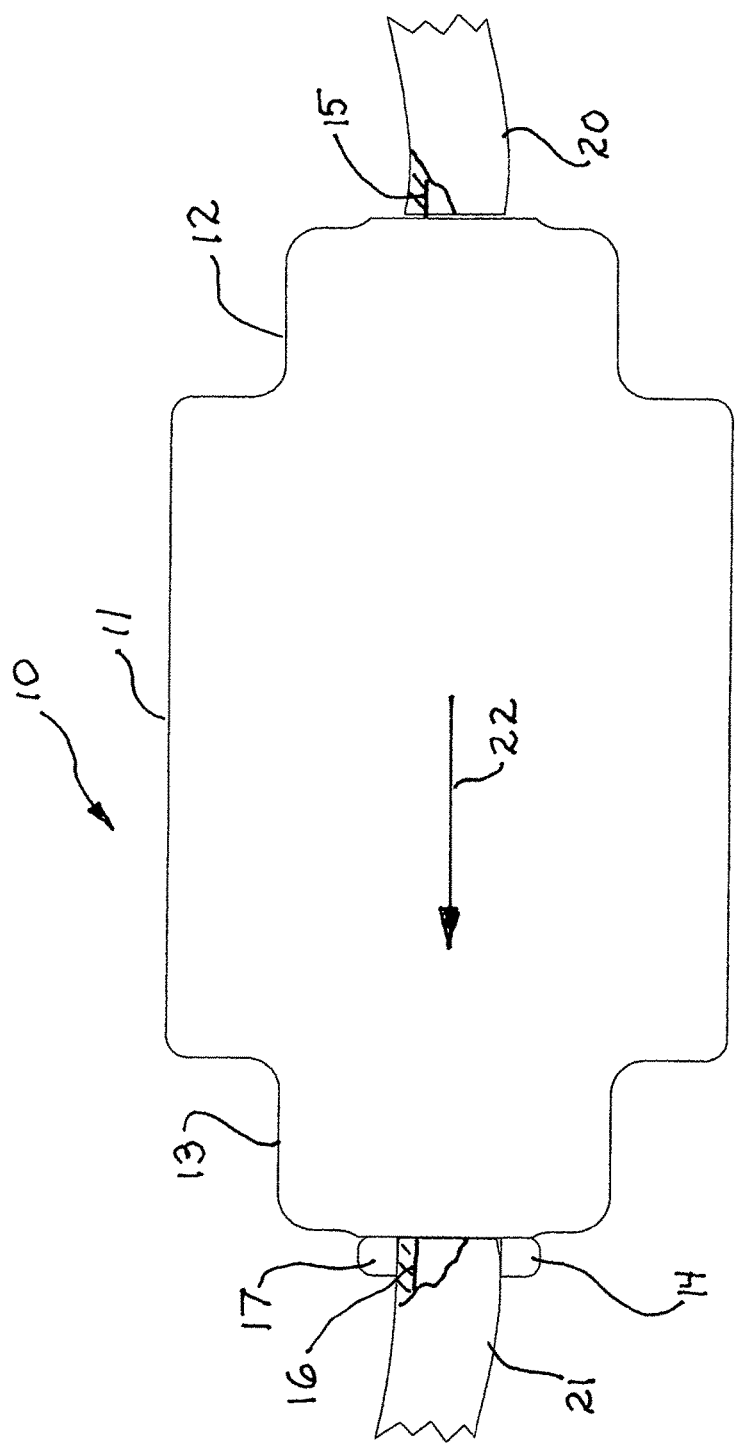
FIG. 2 sets forth a side elevation view of a ventricular assist device constructed in accordance with the present invention.

FIG. 2 sets forth a side elevation view of ventricular assist device 10 which, as described above, defines a generally cylindrical housing 11 supporting a pair of end caps 12 and 13. An input connector 15 is supported by end cap 12 while connector 16 is supported by end cap 13. Also shown in FIG. 2 is the connection of blood flow hoses 20 and 21 joined to input connector 15 and output connector 16 by conventional fabrication.

In operation, a pair of turbine pumps, better seen in FIGS. 5 and 6 below, are operative within ventricular assist device 10 to provide blood flow from hose 20 through housing 11 and outwardly through hose 21. As is set forth and described below in greater, detail a pair of turbine pumps arranged in a series configuration are operative to provide blood flow and, due to the redundancy of turbine pumps, also provides enhanced reliability. In the general design considerations under which ventricular assist device 10 is fabricated, either turbine pump has sufficient capability to be operated to produce a blood flow rate sufficient stain the life of the ventricular assist device recipient. FIG. 2 also shows the position of blood pressure sensors 14 and 17 upon output connector 16. As described below pressure now sensors 14 and 16 are operatively coupled to the controller shown in FIG. 5 to provide operational monitoring of ventricular assist device 10.

Figure 3:
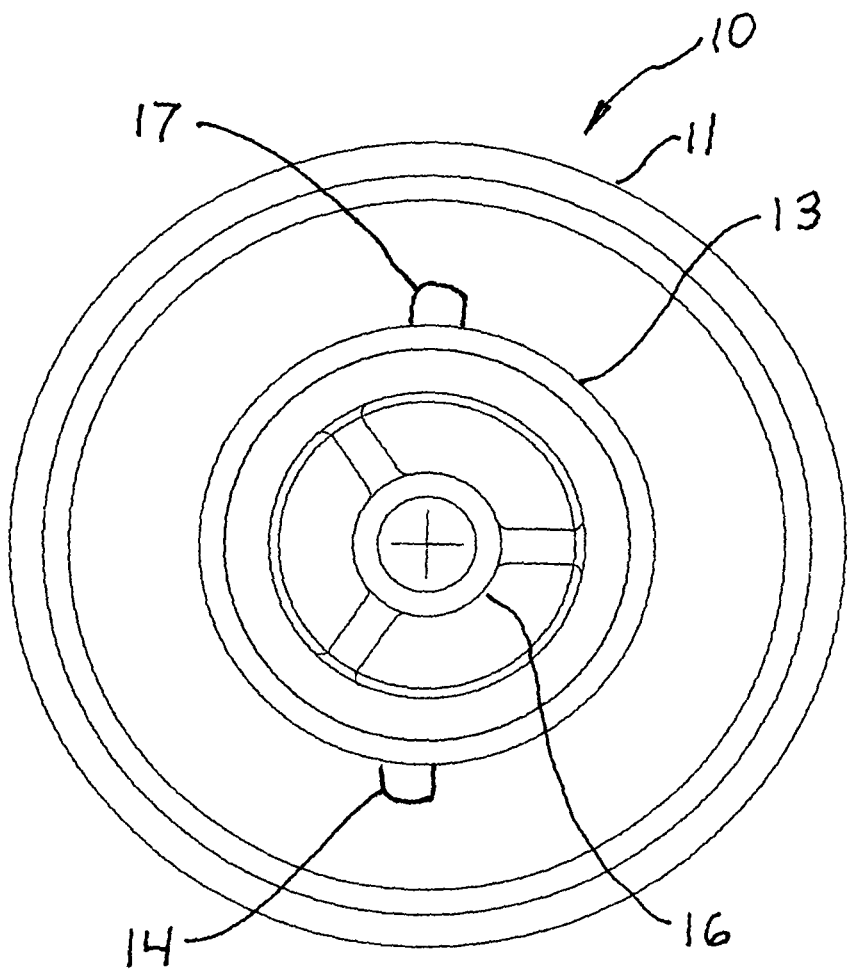
FIG. 3 sets forth an end view of a ventricular assist device constructed in accordance with the present invention.

FIG. 3 sets forth an end view of ventricular assist device 10 showing the concentric arrangement of cylindrical housing 11 and end cap 13. While not seen in FIG. 3, it will be understood that the opposite end of ventricular assist device 10 is substantially identical to the end view shows in FIG. 3. FIG. 3 also shows the position of output connector 16 upon and 13. The generally concentric arrangement of housing 11, end cap 13 and output connector 16 provides the highly desirable "straight-through" blood flow provided by the redundant turbine pumps within ventricular assist device 10.

Figure 4:
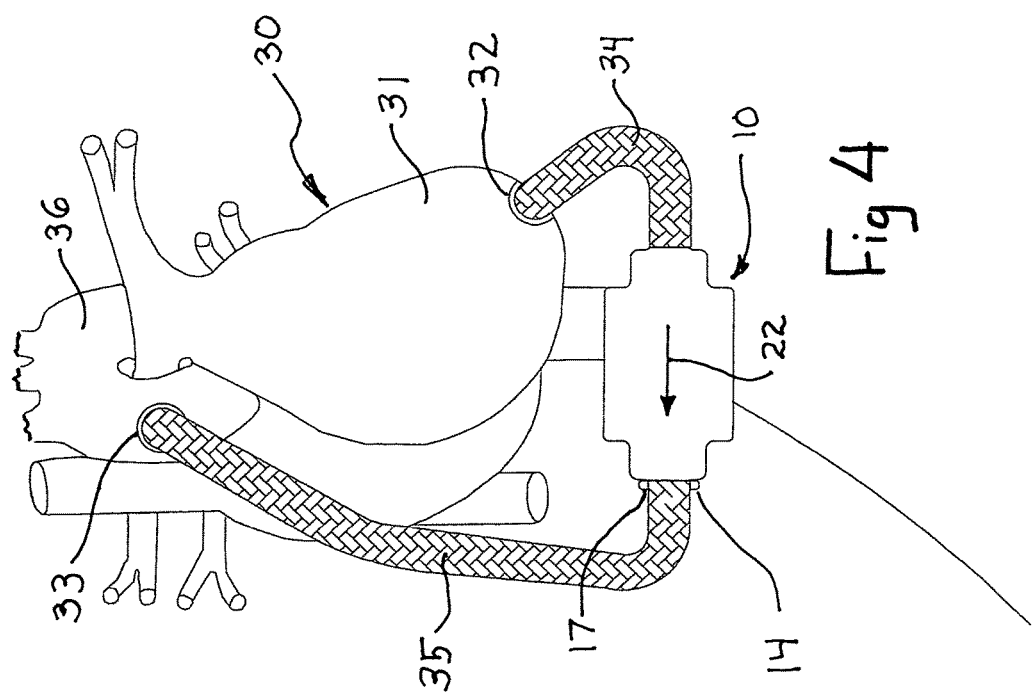
FIG. 4 sets forth a depiction of a ventricular assist device instructed in accordance with the present invention operatively coupled to a human heart.

FIG. 4 sets forth a depiction of ventricular assist device 10 coupled to an illustrative human heart generally referenced by numeral 30. Human heart 30 includes a left ventricle 31 and aorta 36. In the application of ventricular assist device 10 shown in FIG. 4, ventricular assist device 10 is functioning as a left ventricle assist device. The input of ventricular assist device 10 is coupled to the lower portion of left ventricle 31 at a coupling 32 using a hose 34. A hose 35 is coupled to the output connector of ventricular assist device 10 and coupled to aorta 36 of heart 30 at a coupling 33. Couplings 32 and 33 are achieved utilizing conventional medical techniques to provide effective blood transfer and to prevent leakage and other problems. Similarly, hoses 34 and 35 are fabricated of a medically of approved flexible hose construction and may be entirely conventional in fabrication.

In operation, heart 30 will be understood to be beating and attempting to pump blood from left ventricle 31 to aorta 36 and from there outwardly through the arteries of the patient's body. In a typical use of a ventricular assist device performing in the role of a left ventricle assist device shown in FIG. 4, left ventricle 31 is, for some reason, underperforming and an adequate supply of blood is not being pumped into aorta 36. The benefit provided by ventricular assist device 10 in its role as a left ventricle assist device is to provide a supplemental blood flow from left ventricle 31 through hose 34 to ventricular assist device 10. As ventricular assist device 10 is operated blood is pumped in the direction indicated by arrow 22 which is carried by hose 35 to coupling 33 and thereafter flows into aorta 36. This is the basic left ventricle assist performance which greatly improves the blood supply and blood flow for the host patient despite the underperformance of left ventricle 31, or other causes of heart underperformance. In accordance with an important aspect the present invention, increased reliability is provided by ventricular assist device 10 due in part to the redundant dual turbine pump arrangement.

Figure 5:
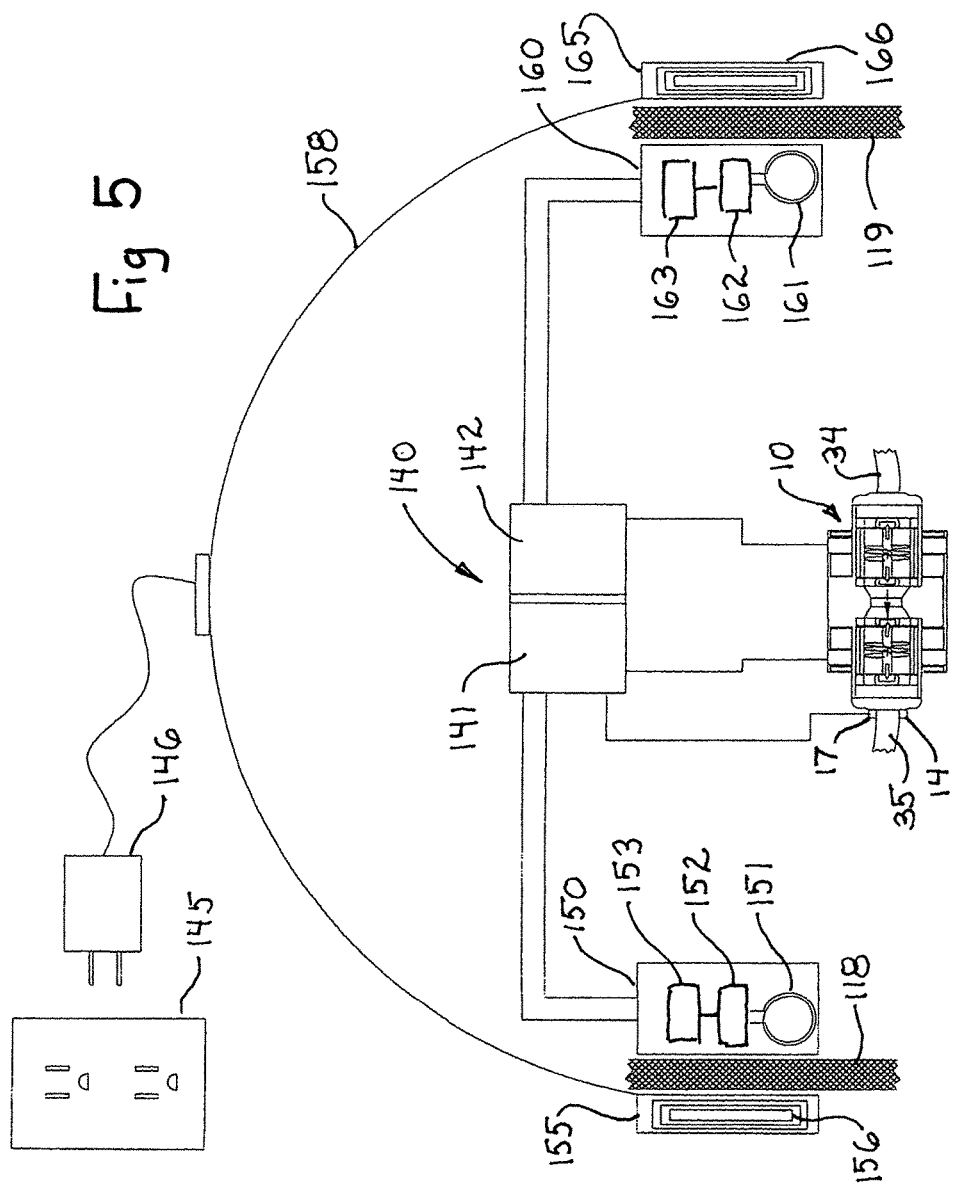
FIG. 5 sets forth a system diagram of a ventricular assist device constructed in accordance with present invention installed within and upon an illustrative human recipient.

FIG. 5 sets forth a system diagram of the present invention ventricular assist device 10 together with supporting apparatus depicting the installation of ventricular assist device 10 within a host patient's body. In the situation represented in FIG. 5, ventricular assist device 10 has been implanted within a host patient's body and is operatively coupled in the manner set forth above in FIG. 4 to the host patient's heart to provide a left ventricle assist device. FIG. 5 further shows microcontroller unit 140 also implanted within the host patient's body. Microcontroller unit 140 is formed of a pair of fully redundant micro controllers 141 and 142. The redundancy of microcontrollers 141 and 142, each able to fully support the operation of ventricular assist device 10, provides a further measure of reliability. Microcontroller unit 140 further includes conventional apparatus (not shown) for communicating to the exterior of the host patient's body in order to provide alarm condition information or other required maintenance of monitoring information to an external unit (not shown). As described above, ventricular assist device 10 includes a pair of sensors 14 and 17 situated at the output of ventricular assist device 10. Sensors 14 and 17 are coupled to redundant microcontrollers 141 and 142. Microcontroller 142 further includes additional sensors supported within ventricular assist device 10 for monitoring the performance of the servo drive apparatus therein. A pair of battery units 150 and 160 are also implanted within the host patient. Battery unit 150 includes a secondary charging coil 151 coupled to a rectifier 152 which, in turn, is coupled to a battery 153. Battery unit 150 is coupled to microcontroller 141. Similarly, battery unit 160 includes a charging coil 161 coupled to a rectifier 162 which, in turn, is coupled to a battery 163. By way of further similarity, battery unit 160 is operatively coupled to microcontroller 142. Thus, microcontroller unit 140, ventricular assist device 10 and battery units 150 and 160 together with appropriate wire connections therebetween are implanted within a host patient body. For purpose of illustration, FIG. 5 shows body segments 118 and 119 which represent the skin and associated tissues of the host patient body beneath which battery units 150 and 160 are implanted. Preferably, units 150 and 160 are implanted near the host patient's mid section and preferably situated just beneath the patient's skin.

A charging belt 158 suitably configured to be worn by the host patient such as at or near the patient's waist supports a pair of charging units 155 and 156. Charging units 155 and 165 include respective primary charging coils 156 and 166. Coils 156 and 166 are coupled to source of alternating current power such as a conventional electrical outlet 145 via a conventional coupling adapter 146.

Figure 6:
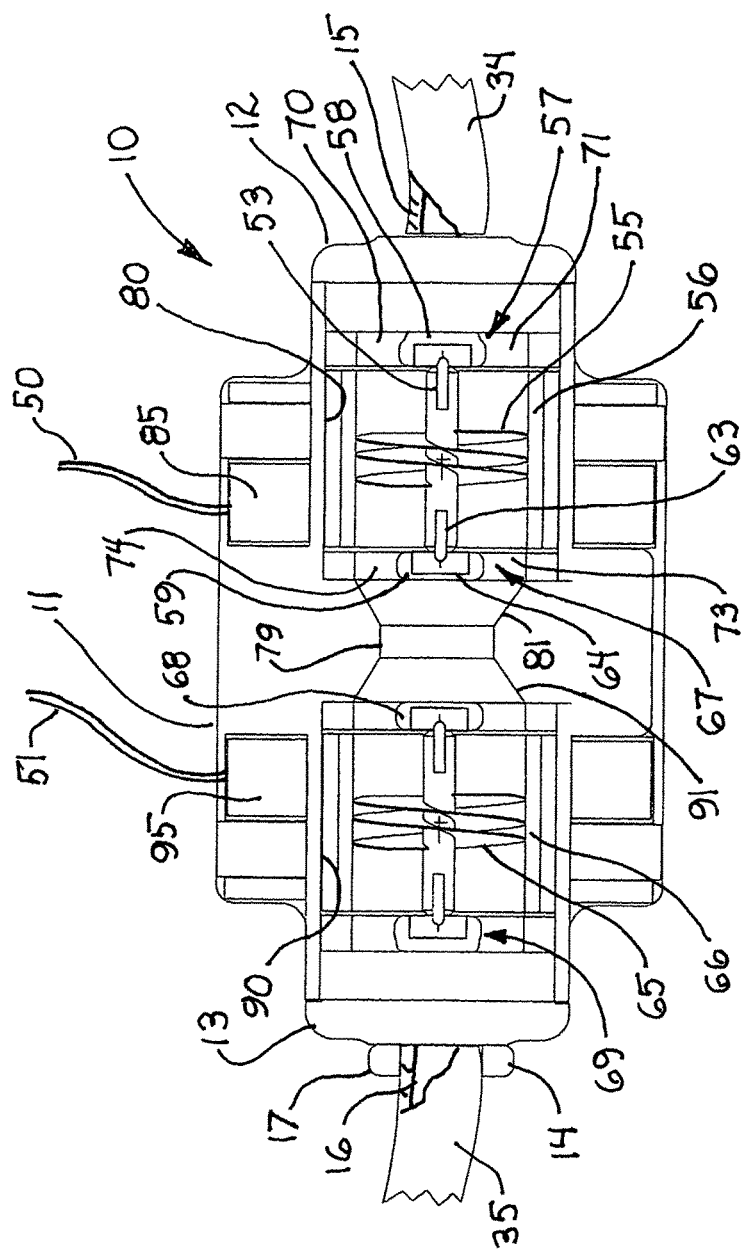
FIG. 6 sets forth a section view of a ventricular assist device constructed in accordance with present invention.

In operation, micro controllers 141 and 142 monitor sensors within ventricular assist device 10 and provide suitable operating power and control to the servo drives supported therein (seen in FIG. 6). Microcontrollers 141 and 142 utilize batteries 153 and 163 for operative battery supply and for power to energize the servo drive apparatus within ventricular assist device 10. The operative power stored within batteries 153 and 163 is provided by inductive charging utilizing charging units 155 and 165. Thus, during convenient periods, the host patient utilizes charging belt 158 by coupling it to power source 145 while wearing belt 158 such that primary charging coils 156 and 166 are positioned on the outside of body portions 118 and 119 respectively. Also, a general alignment is obtained between primary charging coils 156 and 166 and secondary coils 151 and 161 respectively. Electrical power is then inductively coupled through body portions 118 and 119 to induce alternating current power within secondary coils 151 and 161. Rectifiers 152 and 162 convert the alternating current induced in coils 151 and 151 to a direct current power suitable for charging batteries 153 and 163. In this manner, the user is able to replenish the battery energies as required by simply wearing charging belt 158 for a suitable time interval.

Micro controller unit 140 functions using, a pair of fully-redundant fully-interconnected micro controllers 141 and 142, each having the complete capability to control and run ventricular assist device 10 and it's monitoring and charging functions. Thus, microcontrollers 141 and 142 provide inputs for two batteries, inputs for multiple pressure and Hall effect servo sensors and systems capable of monitoring multiple battery charge levels and switch between batteries. The redundancy of microcontrollers 141 and 142 includes configuration of the system such that each microcontroller "sees" all its own inputs and also "sees" all inputs to the other microcontroller. This redundancy includes each microcontroller being capable of making compensating performance adjustments to maintain envelope system performance. However, to avoid "hunting" between the redundant microcontrollers, it is preferred that small pressure variations of each pump be allowed before adjustment is made.

Micro controller unit 140 further includes communication capability, such as a wireless unit, to call, or text remote locations to indicate system anomalies, failures, operating conditions, battery charge levels and other conditions. In addition, microcontroller unit 140 provides the capability to adjust each of microcontrollers 141 and 142 based on pressure readings and to set and maintain preset maximum and minimum pressure envelopes. Microcontroller unit 140 also provides the ability of replicating the pulsetile characteristic of a normal human heart by introducing pre-programmed increases and decreases of pump speed to create pressure surges and lulls.

FIG. 6 sets forth a section view of ventricular assist device 10. Ventricular assist device 10 includes a pair of turbines 55 and 65 in a series arrangement. Turbine 55 is preferably fabricated to provide a helical blade that is progressive to form a helix. Turbine 55 further supports a cylindrical magnetic rotor 56 which is joined to the outer edges of turbine 55. Magnetic rotor 56 supports a plurality of permanent magnets and together with turbine 55 forms a single preferably integrally fabricated rotating component. Thus, for example, it will be recognized that while turbine 55 may be precision-fitted within magnetic rotor 56 due to the cylindrical structure of magnetic rotor 56 thereby forming a single rotating unit, in the preferred fabrication of the present invention magnetic rotor 56 is integrally formed and molded with turbine 55. In either event, it will be recognized that the combined structure of turbine 55 and magnetic rotor 56 forms a single integral rotating unit. The combined structure of magnetic rotor 56 and turbine 55 are rotatably supported within the interior of housing 11 by a pair of bearing supports 57 and 67 positioned on each side of the rotating turbine element. The structure of bearing supports 57 and 67 includes center hubs 58 and 59 supported by a plurality of spokes 70, 71 and 72 (spoke 72 not shown). Within hub 58, a bearing cup 54 is supported which in turn receives one end of a bearing pin 53.

Bearing support 67 is identical to bearing support 57 and thus includes a center hub 59 which receives a bearing cup 64 and bearing pin 63. During assembly, bearing support 67 receives bearing cup 64 and is inserted in turbine receptacle 80 formed in housing 11. Thereafter, bearing pins 64 and 63 are inserted into the support shaft of turbine 55. The combined structure of turbine 55 supporting bearing pins 63 and 64 together with magnetic rotor 56 is then inserted into turbine receptacle 80. Bearing support 57 is then fitted within turbine receptacle 80 such that bearing pin 53 is received within bearing cup 54. Turbine 65 is similarly assembled within turbine receptacle 90. Once both turbine and magnetic rotor combinations have been assembled within housing 11, end caps 12 and 13 are joined to center housing 11 using an attachment such as thermal or sonic welding or other appropriate attachment. Once end caps 12 and 13 are assembled to center housing 11, the structure of ventricular assist device 10 is complete and the resulting pump structure may be described.

More specifically, ventricular assist device 10 includes a center housing 11 defining a pair of turbine receptacles 80 and 90. Receptacles 80 and 90 are aligned coaxially and define cylindrical receptacles. Turbine receptacles 80 and 90 are coupled by a venturi coupling passage formed by a tapered portion 81, a center passage 79 and a tapered portion 91 which are also generally coaxial with turbine receptacles 80 and 90.

Housing 11 further supports a generally cylindrical drive coil array 85 which encircles turbine receptacle 80. Drive coil assembly 85 is coupled to a motor controller such as controller 140 set forth above in FIG. 5. Similarly, housing 11 supports a corresponding drive coil 95 which encircles turbine receptacle 90. Thus, it will be appreciated that ventricular assist device 10 utilizes a pair of turbine pump stages arranged as a series coupled pair. It will be equally well appreciated that each of the two pump stages operative within turbine receptacles 80 and 90 includes the combination of a turbine and a magnetic rotor. The resulting combinations are often referred to in the art as "frameless servo motors". However, it will be apparent to those skilled in the art that other servo motor drive structures may be used to rotate the turbines without departing from the spirit and scope of the present invention. In accordance with an important aspect of the present invention, it will be noted that each of the pump stages may be independently operated and controlled as to speed and output. It will be further apparent to those skilled in the art that the use of pump stages in pairs provides a redundant pump stage arrangement that allows either pump stage to continue to provide blood flow despite a failure of either pump stage.

In operation, the series pair of pump stages of ventricular assist device 10 are driven by drive and control apparatus operative in combination to maintain blood flow. Accordingly, appropriate electrical signals are applied to drive coils 85 and 95 to induce rotation of magnetic rotors 56 and 66 which produces rotation of rotatably supported turbines 55 and 65 along with their respective magnetic rotors 56 and 66. As is described below in greater detail, it will be noted that the rotations of turbines 55 and 65 produce a straight-through flow path between input 15 and output 16. This straight-through flow path is enhanced by the venturi coupling between turbine receptacles 80 and 90 provided by tapered surfaces 81 and 91 together with surface 79. The purpose of the venturi coupling is to increase the flow velocity between the pump turbines and further enhance the blood flow between input 15 and output 16. As a result of the straight-through blood flow thus produced, areas of stagnation and blood pooling within the ventricular assist device are avoided. This, in turn, prevents blood coagulation within the ventricular assist device.

Figure 7:
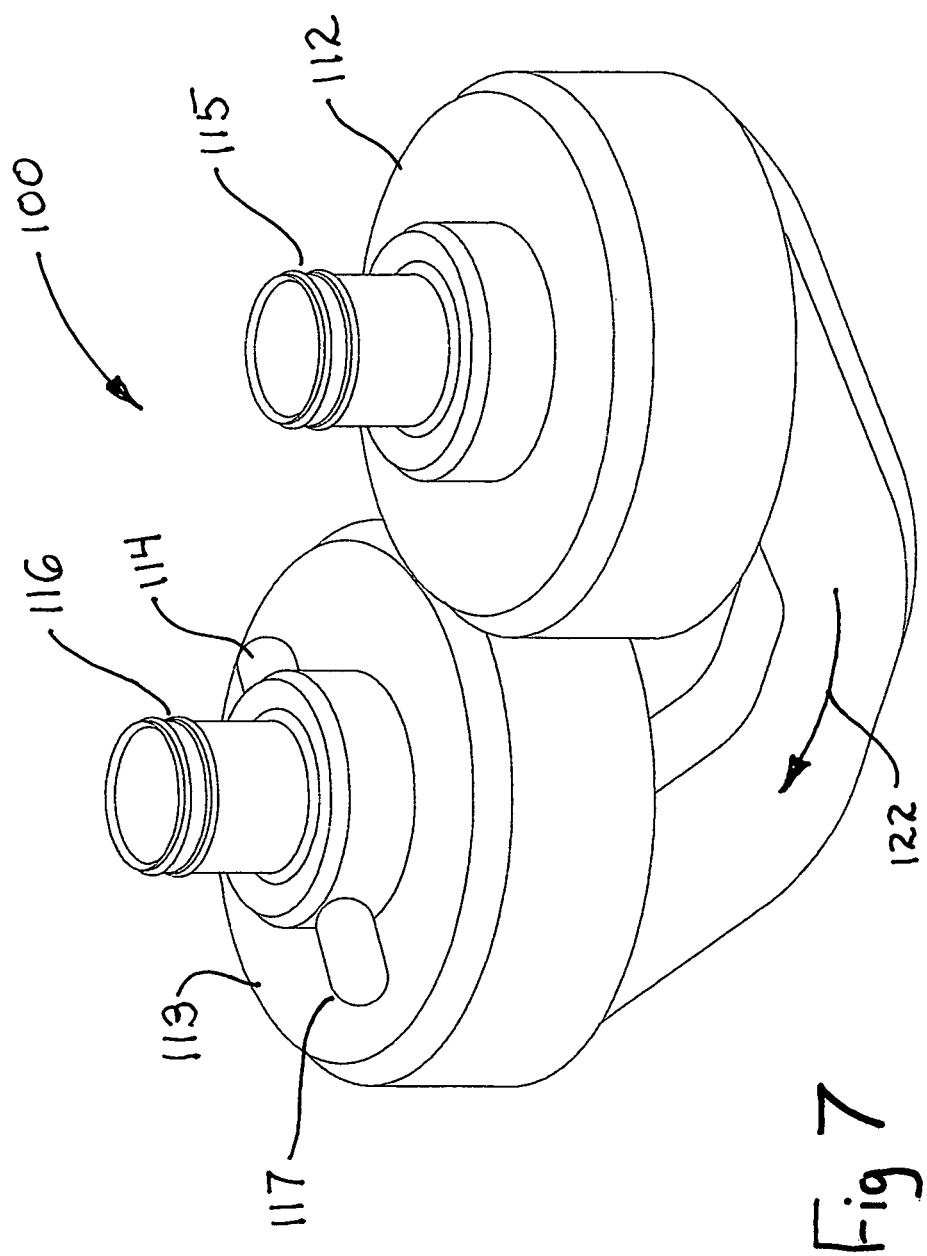
FIG. 7 sets a perspective view of an alternate embodiment of the present invention ventricular assist device.

FIG. 7 sets forth perspective of an alternate embodiment of the present invention ventricular assist device generally referenced by numeral 110. By way of overview, ventricular assist device 110 differs from ventricular assist device 10 shown and described above in that the input connector and output connector are positioned on a common face of the device housing and are oriented in a common direction. To accommodate this connector orientation, the two turbine pumps are positioned in a side-by-side relationship aligned with the respective input and output connectors. The structure is completed by utilizing a curved generally U-shaped venturi coupling passage between the output of the turbine primp that receives blood flow from the input connector and the input to the turbine pump that pumps blood outwardly through the output connector. The result is an equivalent blood flow to the straight-through blood flow which characterizes ventricular assist device 10, described above.

More specifically, ventricular assist device 110 includes a housing 111 (seen in FIG. 8) that provides a protective enclosure for the operative mechanism within ventricular assist device 110. Housing 111 support a pair of end caps 112 and 113. End cap 112 further supports and input connector 115 while end cap 113 further supports an output connector 116. A pair of output pressure sensors 114 and 117 are supported upon output connector 116. In its preferred fabrication, housing 111 and end caps 112 and 113 together with connectors 115 and 116 are formed of a medically approved suitable molded plastic material or the like. By operation set forth below in greater detail, ventricular assist device 110 is operative to pump a flow of blood coupled to input connector 115 to exit at output connector 116. As is better seen below in FIG. 10, conventional hoses 134 and 135 may be coupled to input connector 115 and output connector 116 respectively to provide blood flow which is pumped through ventricular assist device 110. It will be apparent to those skilled in the art that the small compact generally cylindrical shape of ventricular assist device 110 is well adapted to being implanted within a recipient's chest cavity in the manner shown in FIG. 10. It will be further apparent to those skilled in the art that the curved coupling passage structure utilized in ventricular assist device 10 which places input and output connections upon a common face of housing 111 may be particularly advantageous in certain implant environments and conditions. Conversely, it will be apparent to those skilled in the art that in other patient chest cavity environments a straight-through device structure such as ventricular assist device 10 may be advantageous. Accordingly, the present invention ventricular assist device presents alternate embodiments to suit the anticipated variation of chest cavity environments.

Figure 8:
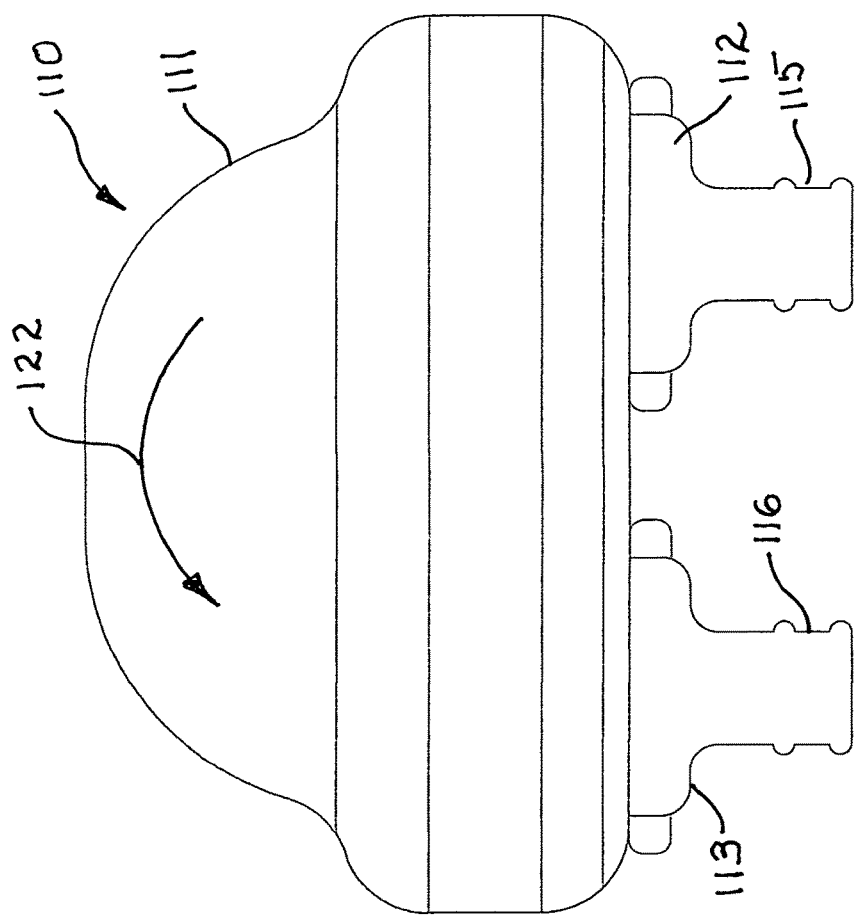
FIG. 8 sets forth a side elevation view of the alternate embodiment of the present invention ventricular assist device set forth in FIG. 7.

FIG. 8 sets forth a side elevation view of ventricular assist device 110 which, as described above, defines a housing 111 supporting a pair of end caps 112 and 113. An input connector 115 is supported by end cap 112 while connector 116 is supported by end cap 113.

In operation, a pair of turbine, pumps, better seen in FIGS. 11 and 12 below, are operative within operative within ventricular assist device 110 to provide blood flow from input 115 through housing 111 and outwardly through output connector 116. As is set forth and described below in greater detail, a pair of turbine pumps arranged in a series configuration is operative to provide blood flow and due to the redundancy of turbine pumps also provides enhanced reliability. In the general design considerations under which ventricular assist device 110 is fabricated, either turbine pump has sufficient capability to be operated to produce a blood flow rate sufficient sustain the life of the ventricular assist device recipient. FIGS. 111 and 112 also shows the position of blood flow pressure sensors 114 and 117 upon output connector 116. As described below, pressure sensors 114 and 117 are operatively coupled to the controller shown in FIG. 11 to provide operational monitoring of ventricular assist device 110.

Figure 9:
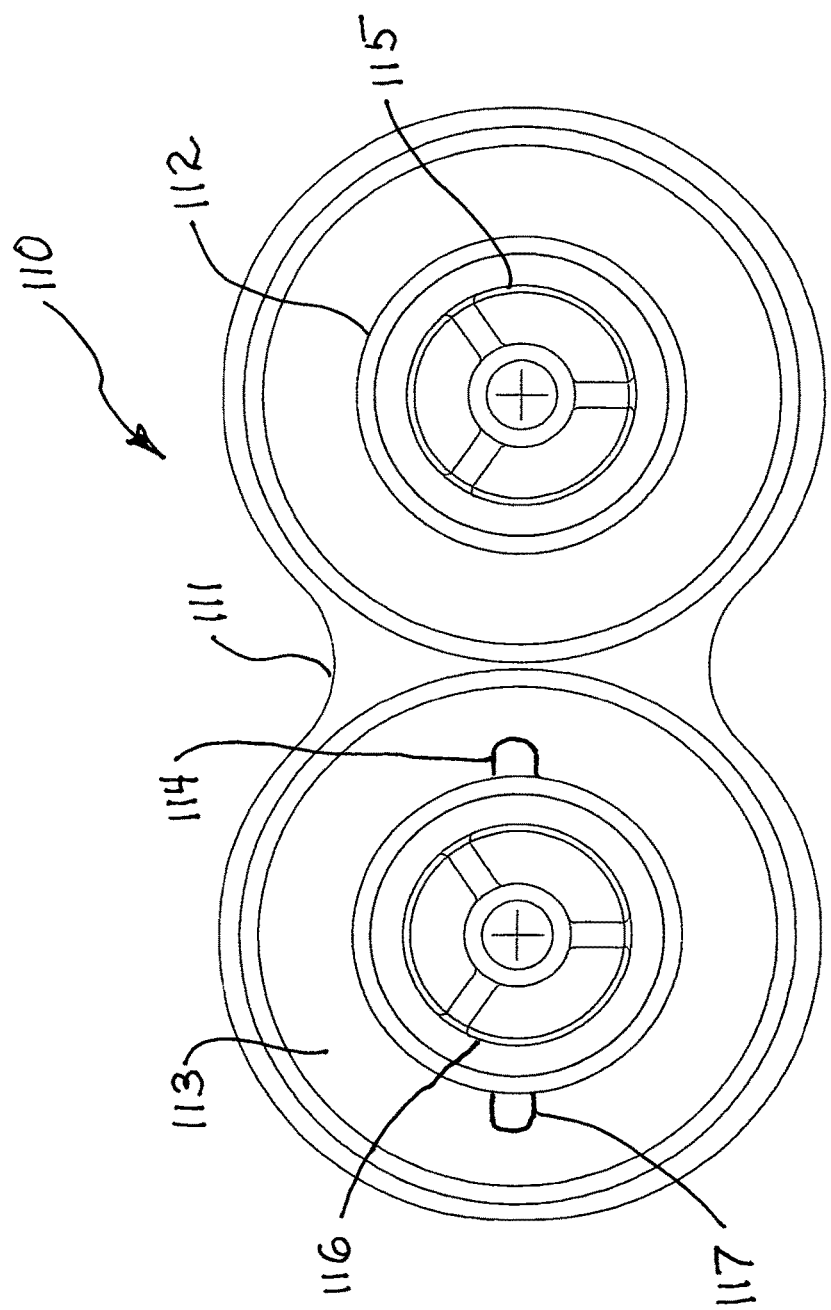
FIG. 9 sets forth a front view of the alternate embodiment of the present invention ventricular assist device show in FIG. 7.

FIG. 9 sets forth an end view of ventricular assist device 110 showing housing 111 supporting an end cap 112 and input connector 115. FIG. 9 also shows the position of output connector 116 upon end cap 113 which are also supported by housing 111. The arrangement of housing 111, end caps 112 and 113 and input connector 115 and output connector 116 provide a blood flow produced by the redundant turbine pumps within ventricular assist device 110 that maintains both connectors on a common housing face while continuing to provide the venturi increased rate of blood flow similar to the above described straight-through blood flow. Pressure sensors 114 and 117 provide blood pressure information to be utilized by the microcontrollers (described below).

Figure 10:
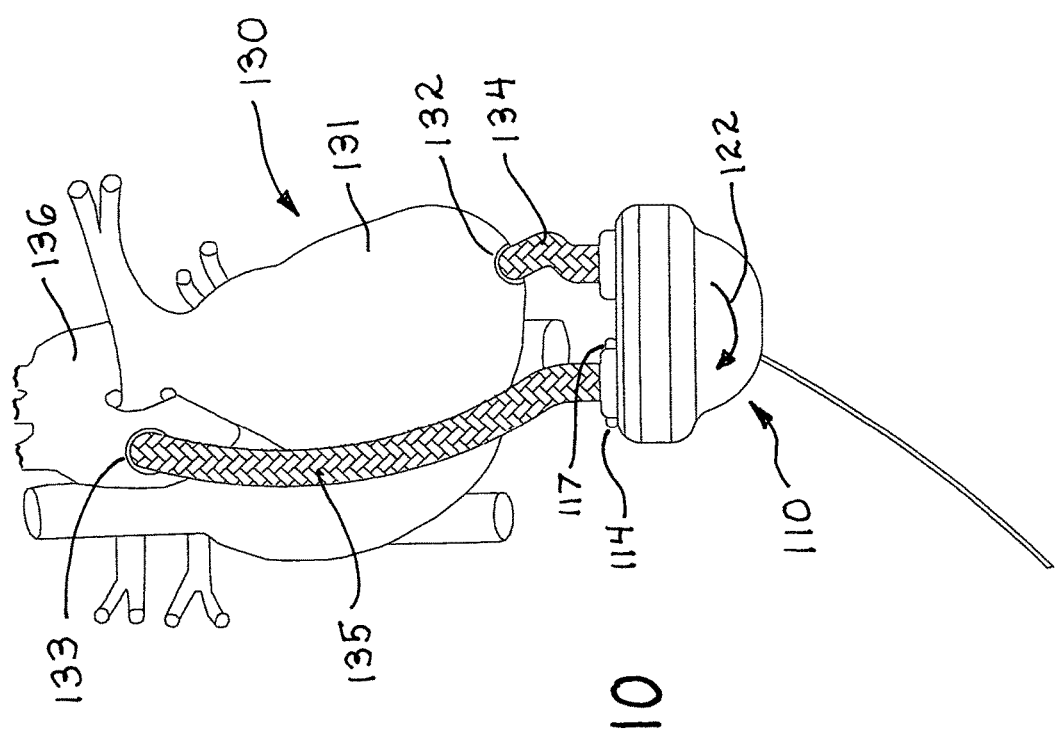
FIG. 10 sets forth a depiction of a ventricular assist device constructed in accordance with the alternate embodiment of the present invention set forth in FIG. 7 operatively coupled to a human heart.

FIG. 10 sets forth a depiction of ventricular assist device 110 coupled to an illustrative human heart generally referenced by numeral 130. Human heart 130 includes a left ventricle 131 and an aorta 136. In the application of ventricular assist device 110 shown in FIG. 10, ventricular assist device 110 is functioning as a left ventricle assist device. Thus, the input of ventricular assist device 110 is coupled to the lower portion of left ventricle 131 at a coupling 132 using a hose 134. A hose 135 is coupled to the output connector of ventricular assist device 110 and is coupled to aorta 136 of heart 130 at a coupling 133. Couplings 132 and 133 are achieved utilizing conventional medical techniques to provide effective blood transfer and to prevent leakage and other problems. Similarly hoses 134 and 135 are fabricated of a medically of approved flexible hose construction and may be entirely conventional in fabrication.

In operation, heart 130 will be understood to be beating and attempting to pump blood from left ventricle 131 to aorta 136 and from there outwardly through the arteries of the patient's body. In a typical use of a ventricular assist device in the role of a left ventricle assist device shown FIG. 10, left ventricle 131 is, for some reason, underperforming and an adequate supply of blood is not being pumped into aorta 136. The benefit provided by ventricular assist device 110 in its role as a ventricle assist device is to provide a supplemental blood flow from left ventricle 131 through hoses 134 and 135 to aorta 136. As ventricular assist device 110 is operated, blood is pumped in the direction, indicated by arrow 122 which is carried by hose 135 to coupling 133 and thereafter flows into aorta 136. This is the basic left ventricle assist performance which greatly improves the blood supply and blood flow throughout the circulatory system the host patient, Thus, despite the underperformance of left ventricle 131, or other causes of heart underperformance, the host patient is sustained. In accordance with an important aspect the present invention ventricular assist device 110, blood flow velocity is maintained and blood pooling or stagnating is prevented throughout ventricular assist device 110 as well as hoses 134 and 135. The reliability of this vital blood flow is greatly improved due, in large part to the redundant dual turbine pumps and their series arrangement provided by the invention. Even in the event of a failure of one of the turbine pumps, the remaining turbine pump continues and also increases output to compensate for the loss one turbine pump.

Figure 11:
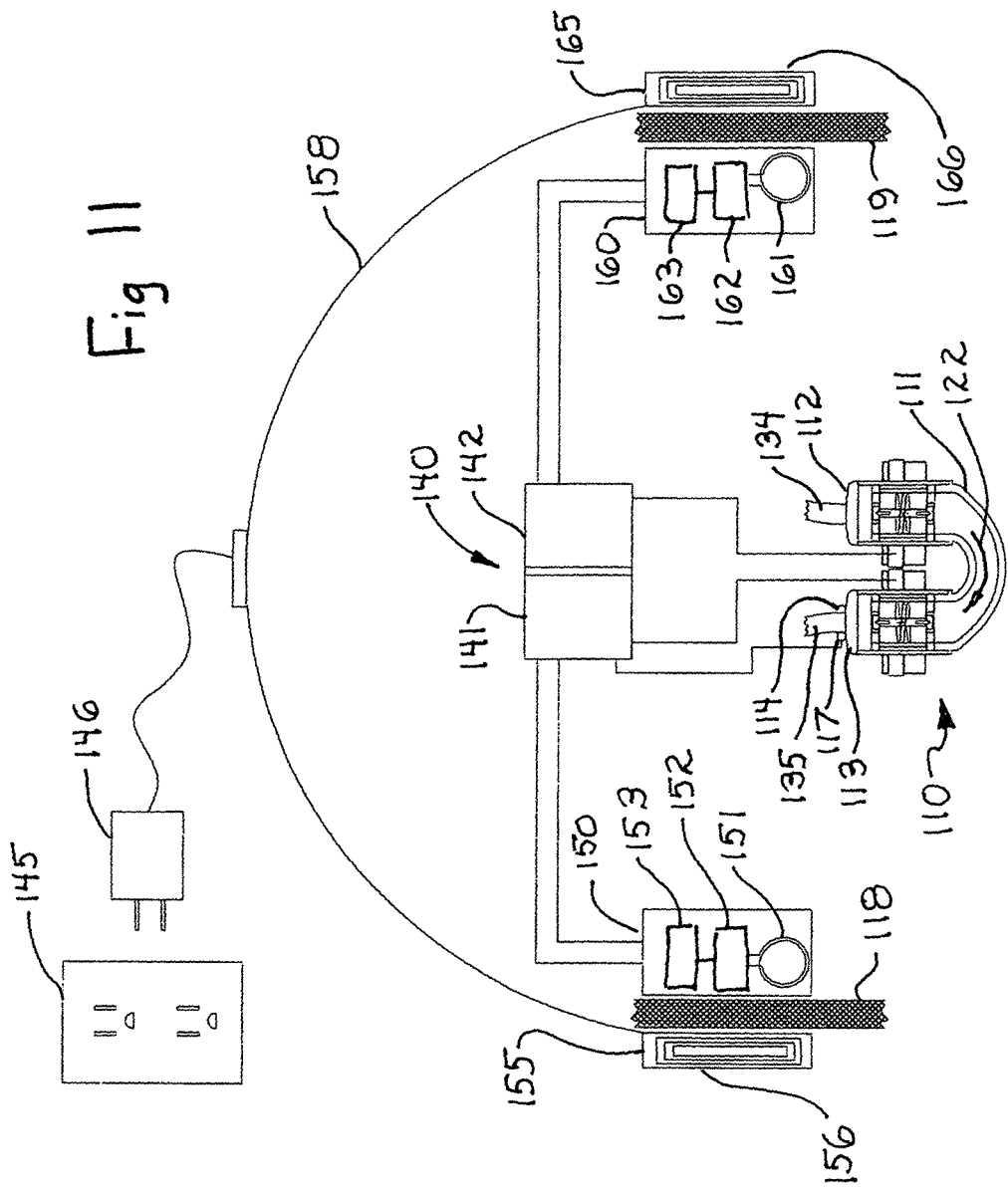
FIG. 11 sets forth a system diagram of a ventricular assist device constructed in accordance with the alternate embodiment of the present invention set forth in FIG. 7 installed within and upon an illustrative human recipient.

FIG. 11 sets forth a system diagram of the present invention ventricular assist device 110 together with supporting apparatus depicting the installation of ventricular assist device 110 within a host patient's body. In the situation represented in FIG. 11, ventricular assist device 110 has been implanted within a host patient's body and is operatively coupled to the heart in the manner set forth above in FIG. 10 to provide a left ventricle assist device. FIG. 11 further shows a microcontroller unit 140 also implanted within the host patient's body. Microcontroller unit 140 is formed of a pair of fully redundant micro controllers 141 and 142. The redundancy of microcontrollers 141 and 142, with each able to fully support the operation of ventricular assist device 110 provides a further measure of reliability. Microcontroller unit 140 further includes conventional apparatus (not shown) for communicating to the exterior of the host patient's body in order to provide alarm condition information or other required maintenance or monitoring information to an external unit (not shown). As described above, ventricular assist device 110 includes a pair of sensors 114 and 117 situated at the output of ventricular assist device 110. Sensors 114 and 117 are coupled to redundant microcontrollers 141 and 142. Microcontroller 142 further includes additional sensors supported within ventricular assist device 110 for monitoring the performance of the servo drive apparatus therein. A pair of battery units 150 and 160 are also implanted within the host patient. Battery unit 150 includes a secondary charging coil 151 coupled to a rectifier 152 which in turn is coupled to a battery 153. Battery unit 150 is coupled to microcontroller 141. Similarly, battery unit 160 includes a charging coil 161 coupled to a rectifier 162 which in turn is coupled to a battery 163. By way of further similarity, battery unit 160 is operatively coupled to microcontroller 142. Thus, microcontroller unit 140, ventricular assist device 110 and battery units 150 and 160 together with appropriate wire connections therebetween are implanted within a host patient body. For purpose of illustration, FIG. 11 shows body segments 118 and 119 which represent the skin and associated tissues of the host patient body beneath which battery units 150 and 160 are implanted. Preferably, units 150 and 160 are implanted near the host patient's mid section and preferably situated just beneath the patient's skin.

A charging belt 158 suitably configured to be worn by the host patient such as at or near the patient's waist supports a pair of charging units 155 and 156. Charging units 155 and 165 include respective primary charging coils 156 and 166. Coils 156 and 166 are coupled to source of alternating current power such as a conventional electrical outlet 145 via a conventional coupling adapter 146.

Figure 12:
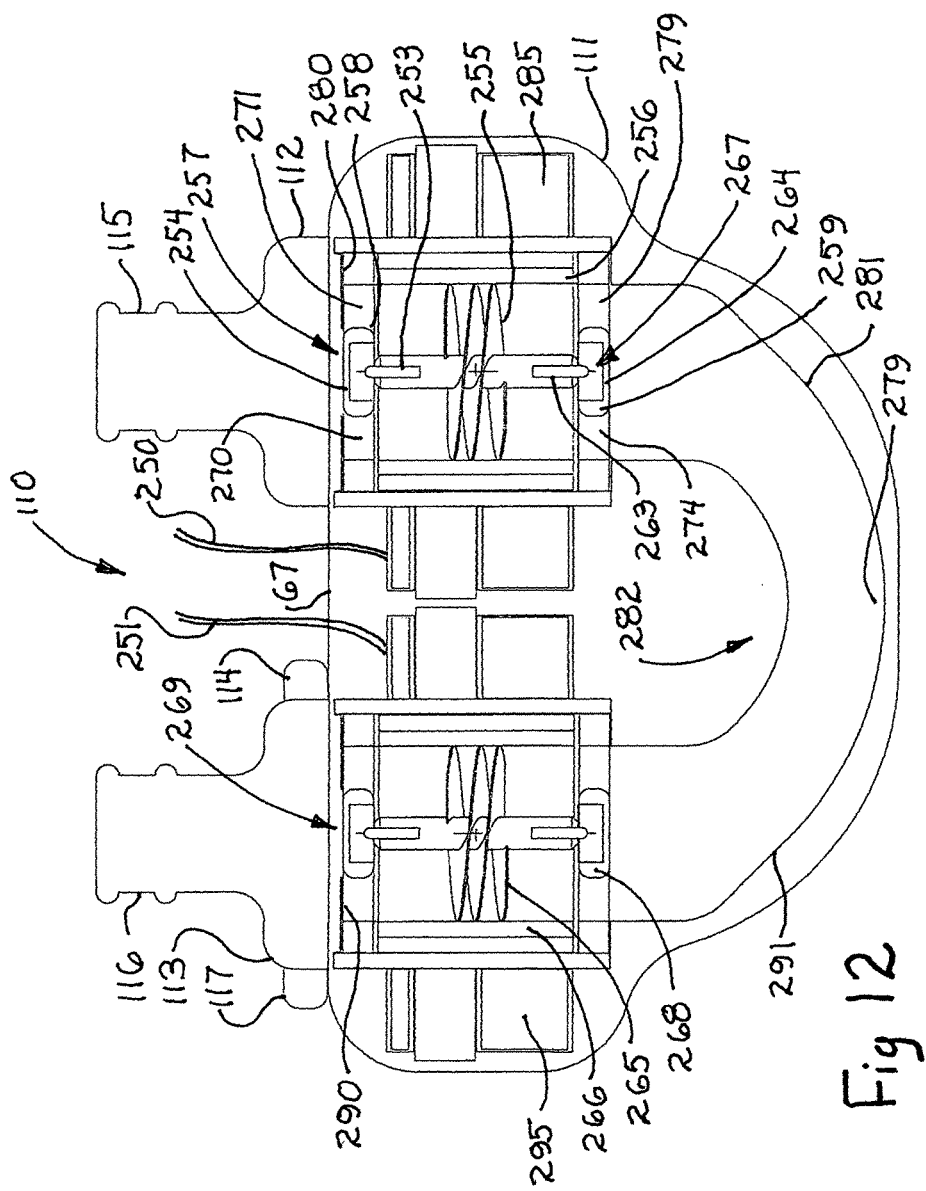
FIG. 12 sets forth a section view of the alternate embodiment of the preset invention ventricular assist device set forth in FIGS. 7.

In operation, micro controllers 141 and 142 monitor sensors within ventricular assist device 110 and provide suitable operating power and control to the servo drives supported therein (seen in FIG. 12). Microcontrollers 141 and 142 utilize batteries 153 and 163 for operative battery supply and for power to energize the servo drive apparatus within ventricular assist device 110. The operative power stored within batteries 153 and 163 is provided by inductive charging utilizing charging units 155 and 165. Thus, during convenient periods, the host patient utilizes charging belt 158 by coupling to power source 145 while wearing belt 158 such that primary charging coils 156 and 166 are positioned on the outside of body portions 118 and 119 respectively such that general alignment is obtained between primary charging coils 156 and 166 and secondary coils 151 and 161 respectively. Electrical power is then inductively coupled through body portions 118 and 119 to induce alternating current power within secondary coils 151 and 161. Rectifiers 152 axed 162 convert the alternating current induced in coils 151 and 161 to a direct current power suitable for charging batteries 153 and 163, in this manner, the user is able to replenish the battery energy as required by simply wearing charging belt 158 for a suitable time interval.

Micro controller unit 140 functions using a pair of fully-redundant fully-interconnected micro controllers 141 and 142, each having the complete capability to control and run the entire ventricular assist device 110 and it's monitoring and charging functions. Thus, microcontrollers 141 and 142 provide inputs for two batteries, inputs for multiple pressure and Hall effect servo sensors and systems capable of monitoring multiple battery charge levels and between batteries. The redundancy of microcontrollers 141 and 142 includes configuration of the system such that each microcontroller "sees" all its own inputs and also "sees" all inputs to the other micro controller. This redundancy includes each microcontroller being capable of making compensating performance adjustments to maintain envelope system performance. However, to avoid "hunting" between the redundant microcontrollers, it is preferred that small pressure variations of each pump be allowed before adjustment is made.

Micro controller unit 140 further includes communication capability, such as a wireless unit, to call, or text remote locations to indicate system anomalies, failures, operating conditions, battery charge levels and other conditions. In addition, micro controller unit 140 provides the capability to adjust each of micro controllers 141 and 142 based on pressure readings and to set and maintain preset maximum and minimum pressure envelopes. Micro controller unit 140 also pro the ability of replicating the pulsetile operation characteristic of a normal human heart by introducing pre-programmed increases and decreases of pump speed to create pressure surges and lulls.

FIG. 12 sets forth a section view of ventricular assist device 110 supported within housing 111. Housing 111 defines a common surface 67. Ventricular assist device 110 includes a pain of turbines 255 and 265 in a series arrangement. Turbines 255 and 265 are identical in fabrication and operation. Accordingly, the descriptions and operation that describe turbine 255 will be understood to be equally descriptive of and apply equally well to turbine 265. Turbine 255 is preferably fabricated to provide a helical blade progressive to form a helix. Turbine 255 further supports a cylindrical magnetic rotor 256 which is joined to the outer edges of turbine 255. Magnetic rotor 256 supports a plurality of permanent magnets and together with turbine 255 forms a single preferably integrally fabricated rotating component. Thus, for example, it will be recognized that while turbine 255 may be precision-fitted within magnetic rotor 256 due to the cylindrical structure of magnetic rotor 256 to form a single rotating unit. In the preferred fabrication of the present invention magnetic rotor 256 is integrally formed and molded with turbine 255. In either event, it will be recognized that the combined structure of turbine 255 and magnetic rotor 256 forms a single integral rotating unit. The combined structure of magnetic rotor 256 and turbine 255 are rotatably supported within the interior of housing 111 by a pair of bearing supports 257 and 267 positioned on each side of the rotating turbine element. The structure of bearing supports 257 and 267 includes center hubs 258 and 259 supported by a plurality of spokes 270, 271 and 272 (spoke 272 not shown). Within hub 258, a bearing cup 254 is supported which in turn receives one end of a bearing pin 253.

Bearing support 267 is identical to bearing support 257 and thus includes a center hub 259 which receives a bearing cup 264 and bearing pin 263. During assembly, bearing support 267 receives bearing cup 264 and is inserted in turbine receptacle 280 formed in housing 111. Thereafter, bearing pins 253 and 263 are inserted into the support shaft of turbine 255. The combined structure of turbine 255 supporting bearing pins 263 and 264 together with magnetic rotor 256 is then inserted into turbine receptacle 280. Bearing support 257 is then fitted within turbine receptacle 280 such that bearing pin 253 is received within bearing cup 254. Turbine 265 is assembled within turbine receptacle 290 in the same manner. Once both turbine and magnetic rotor combinations have been assembled within housing 111, end caps 112 and 113 are joined to center housing 111 using an attachment such as thermal or sonic welding or other appropriate attachment. Once end caps 112 and 113 are assembled to 111, the structure of ventricular assist device 110 is complete and the resulting pump structure may be described.

More specifically, ventricular assist device 110 includes a 111 defining a pair of turbine receptacles 280 and 290. Receptacles 280 and 290 are aligned in a parallel relationship and define cylindrical receptacles. Turbine receptacles 280 and 290 are coupled by a generally U-shaped curved venturi coupling passage 281 formed by a curved narrowing tapered portion 281, a center venturi passage 279 and a curved tapered expanding portion 291. As a result, curved coupling passage 281 flows blood from the output of turbine 255 to the input of turbine 265 at an increased flow rate caused by the venturi effect.

Housing 111 further supports a generally cylindrical drive coil array 285 which encircles turbine receptacle 280. Drive coil assembly 285 is coupled to a motor controller such as controller 140 set forth above in FIG. 11. Similarly, housing 111 supports a corresponding drive coil 295 which encircles turbine receptacle 290. Thus, it will be appreciated that ventricular assist device 110 utilizes a pair of turbine pump stages arranged as a series coupled pair. It will be equally well appreciated that each of the two pump stages operative within turbine receptacles 280 and 290 includes the combination of a turbine and, a magnetic rotor. The resulting combinations are often referred to in the art as "frameless servo motors". However, it will be apparent to those skilled in the art that other motor drive structures may be used to rotate the turbines without departing from the spirit and scope of the present invention. In accordance with an important aspect of the present invention, it will be noted that each of the pump stages may be independently operated and controlled as to speed and output. It will be further apparent to those skilled in the art that the use of pump stages in pairs provides a redundant pump stage arrangement that allows either pump stage to continue to provide blood flow despite a failure of either pump stage.

In operation, the series pair of pump stages of ventricular assist device 110 are driven by drive and control apparatus operative in combination to maintain blood flow. Accordingly, appropriate electrical signals are applied to drive coils 285 and 295 to induce rotation of magnetic rotors 256 and 266 which produces rotation of the rotatably supported turbines 255 and 265 along with their respective magnetic rotors 255 and 266. As is described below in greater detail, it will be noted that the rotations of turbines 255 and 265 produce an increased velocity flow path between input 115 and output 116. This flow path is enhanced by the venturi coupling between turbine receptacles 280 and 290 provided by narrowing portion 281 and expanding portion 291 venturi narrows 279. The purpose of the venturi coupling is to increase the flow velocity between the pump turbines and further enhance the blood flow between input 115 and output 116. As a result of the increased velocity blood flow thus produced, areas of stagnation and blood pooling, within the ventricular assist device are avoided. This, in turn, prevents blood coagulation within the ventricular assist device.

Figure 13:
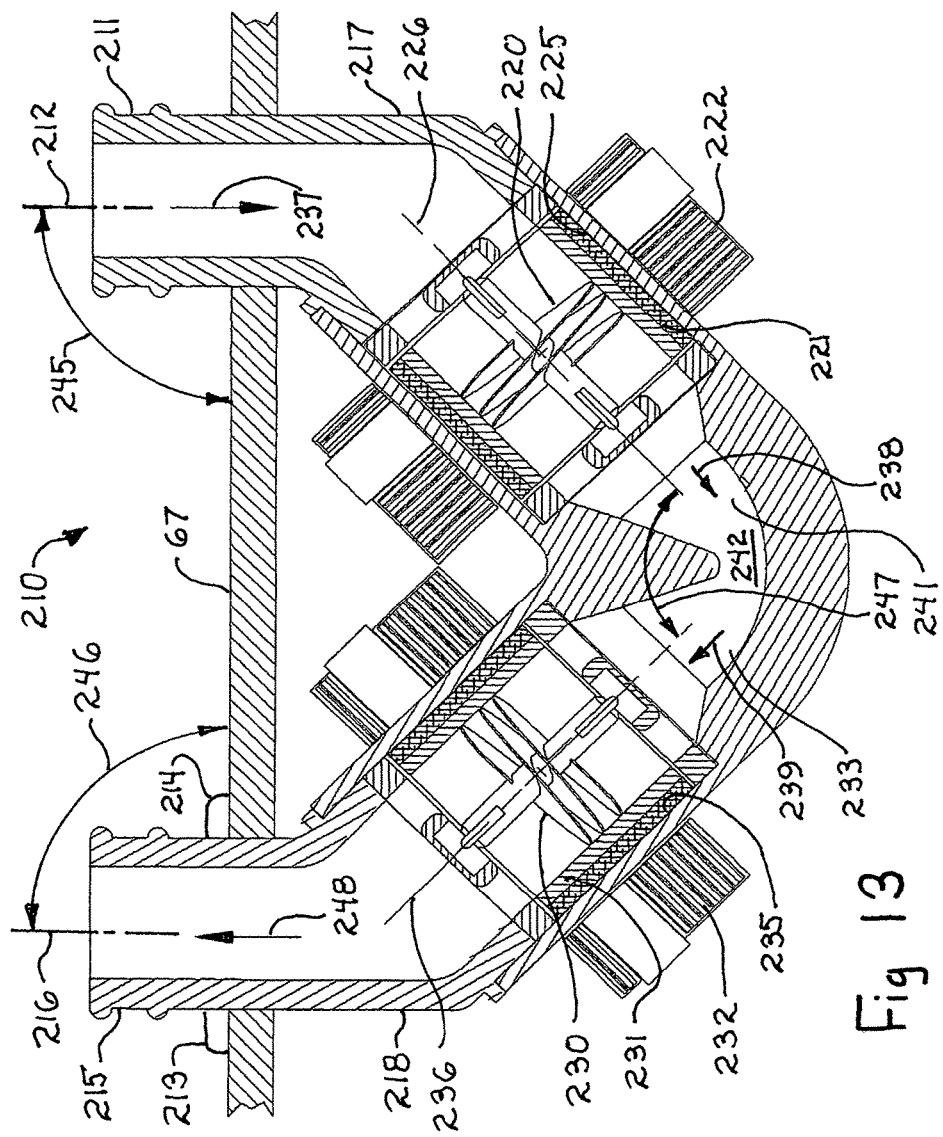
FIG. 13 sets forth a section view of a still further alternate embodiment of the present invention ventricular assist device illustrating an angular coupling passage and angularly disposed turbine pumps.

FIG. 13 sets forth a section view of a still further alternate embodiment of the present invention ventricular assist device. By way of overview, it will be apparent that the alternate embodiment shown in FIG. 13 is identical to the above described embodiments in that a pair of series coupled (with respect to blood flow) turbine pumps are operative to draw blood into an input connector, flow blood through a coupling passage, that preferably includes a venturi portion, and thereafter discharge the blood flow through and output connector. In the embodiment shown in FIG. 13 the input and output connectors are supported upon a common surface of the ventricular assist device housing and preferably emerge at approximately right angles to the common surface. The embodiment shown in FIG. 13 differs from the embodiments set forth above in that the coupling passage defines a generally V-shaped blood flow.

More specifically, FIG. 13 sets forth an alternate embodiment of the present invention ventricular assist device generally referenced by numeral 210. Ventricular assist device 210 is shown joined to a common surface 67 which will be understood to comprise a generally planar surface of the housing not shown) within which ventricular assist device 210 is enclosed. Thus, ventricular assist device 210 includes an input connector 211 defining an input connector axis 212 and an output connector 215 defining an output connector axis 216. Collectors 211 and 215 preferably define respective right angles 245 and 246 with respect to common surface 67. Ventricular assist device 210 includes a turbine 220 rotatably supported within a turbine receptacle 225. Turbine 220 is rotatably supported within turbine receptacle 225 and is rotatable about a turbine center axis 226. A magnetic rotor 221 is rotatably supported upon turbine 220 and is rotatable therewith. A drive coil assembly 222 is supported upon turbine receptacle 225 and provides electromagnetic energy which causes turbine 222 rotate and provide the above described blood pumping action. The structure and operation of turbine 220 is identical to the structure and operation of turbine 255 set forth above in FIG. 12.

Ventricular assist device 210 further includes a turbine 230 rotatably supported within turbine receptacle 235 and rotatable about an axis 236. Turbine 230 further includes a magnetic rotor 231. A drive coil assembly 232 encircles turbine receptacle 235 and provides electromagnetic energy which rotates turbine 230. As mentioned above with respect to turbine 220, it will be understood that turbine 230 together with its support structure and drive coil assembly are substantially identical to the above described turbine pumps, such as turbine pump 255 shown in FIG. 12.

Ventricular assist device 210 further includes a generally V-shaped coupling passage 240 which couples blood flow from the output of turbine 220 the input of turbine 230. Coupling passage 240 includes a narrowing portion 241 followed by a venturi portion 242 and an expanding portion 233. Venturi portion 242 performs the same increase of blood flow rate described above to avoid stagnation and blood clotting problems. To accommodate the substantially perpendicular angular relationship between input connector 211 and common surface 67, the interior end of input connector 211 defines an angle 217. Similarly, and for the same reason, output connector 215 includes an angle 218 at its interior end. Turbine axes 226 and 236 define a relative angle 247 therebetween which, in the preferred fabrication of the present invention embodiment of FIG. 13, is a right angle. However, it will be apparent to those skilled in the art, that the angular relationship between the respective axes of turbines 220 and 230 may define different angles without departing from the spirit and scope of the present invention.

In operation, blood flows inwardly through input connector 211 through turbine 220 in the direction indicated by arrow 238. Thereafter, blood flows through venturi portion 242 of coupling passage 240 in the direction indicated by arrow 239. Blood then flows through turbine 230 outwardly, the direction indicated by arrow 248, through output connector 215.

What has been shown is a dual stage redundant impeller ventricular assist device. Within the housing of the device a pair of electrically-driven impeller drive motors facilitate the pumping of blood from one portion of the circulatory system to another portion of the circulatory system, such as from the lower left ventricle to the aorta. The use of dual pump drives for the pump turbines configured to provide complete pump redundancy should a pump fail. In such case, the remaining operative motor/pump drives the turbines coupled thereto with sufficient capability and circulation to, maintain life in the recipient until remedial inter intervention may be performed. The output from the pump support a sensor coupled to a dual microprocessor drive controller. Each processor drive controller is operative coupled to both of the redundant pump drive motors. Sensors are also provided to monitor the operation of each pump system. A pair of battery modules each including an inductively coupled charging device are implanted within the patient abdomen and operatively coupled to the processor controller and the drive motors. A pair of inductive battery charging modules are supported upon an abdominal belt and coupled to a source of operative electrical power. Battery charging is accomplished by inductive coupling through the body tissue between the external charging modules and the implanted battery and charger apparatus. The dual redundant micro controller is also implanted within the recipient's body.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:
1. A ventricular assist device comprising:

a housing having an input, an output and a coupling passage;

a first turbine pump operative to flow blood from said input, through said coupling passage and through said output; and a second turbine pump, separate from and independent of said first turbine pump, operative to flow blood from said input, through said coupling passage and through said output, said coupling passage within said housing coupled between said first turbine pump and said second turbine pump and defining a narrowing portion, a venturi portion and an expanding portion and said first and said second turbine pumps being arranged in a series blood and flow and said first turbine pump is coupled to said narrowing portion of said coupling passage and said second turbine pump is coupled to said expanding portion of said coupling passage, wherein said housing defines a pair of turbine receptacles and wherein said first and second turbine pumps each include:

a respective turbine receptacle:

a turbine rotatably supported within said turbine receptacle:

a magnetic rotor rotatable with and supported by said turbine and a drive coil supported within said housing and encircling said turbine receptacle and said turbine and said magnetic rotor.

2. The ventricular assist device set forth in claim 1 wherein said turbines each include:

a turbine shaft having bearings at opposed ends thereof; and a helical turbine blade supported upon and extending from said turbine shaft defining an outer edge.

3. The ventricular assist device set forth in claim 2 wherein each of said magnetic rotors is cylindrical and defines a respective interior surface and wherein each of said of turbine blades receives said respective interior surface to join said magnetic rotor to said turbine blade.

4. A ventricular assist device comprising:

a housing having an input, an input turbine receptacle, an output, an output turbine receptacle and a coupling passage between said input turbine receptacle and said output turbine receptacle, said input, said input turbine receptacle, said output, said output turbine receptacle and said coupling passage being generally coaxial;

a first turbine pump supported within said input turbine receptacle operative to flow blood from said input through said coupling passage and through said output; and a second turbine pump supported within said output turbine receptacle, separate from and independent of said first turbine pump, operative to flow blood from said input through said coupling passage and through said output, wherein said first and second, turbine pumps are each supported within a respective turbine receptacle and each include:

a turbine rotatably supported within its respective turbine receptacle:

a magnetic rotor rotatable with and supported by said turbine; and a drive coil supported within said housing and encircling said respective turbine receptacle and said turbine and said magnetic rotor.

5. The ventricular assist device set forth in claim 4 wherein said housing is molded and wherein said drive coils are molded into said housing.

6. The ventricular assist device set forth in claim 5 wherein said turbines each include:

a turbine shaft having bearings at opposed ends thereof; and a helical turbine blade supported upon and extending from said turbine shaft and defining a turbine blade outer edge.

7. The ventricular assist device set forth in claim 6 wherein said magnetic rotors are cylindrical and define a respective interior surface and wherein each said turbine blade outer edge of said each turbine blade receives said respective interior surface to join said magnetic rotor to said turbine blade.

8. A ventricular assist device comprising:

a housing having an input, an output and a coupling passage;

a first turbine pump operative to flow blood from said input, through said coupling passage and through said output; and a second turbine pump, separate from and independent of said first turbine pump, operative to flow blood from said input, through said coupling passage and through said output, said coupling passage within said housing coupled between said first turbine pump and said second turbine pump and defining a narrowing portion, a venturi portion and an expanding portion and said first and said second turbine pumps being arranged in a series blood and flow and said first turbine pump is coupled to said narrowing portion of said coupling passage and said second turbine pump is coupled to said expanding portion of said coupling passage, wherein said coupling passage is curved and wherein said input and said output are arranged in a side-by-side position.

9. The ventricular assist device set forth in claim 8 wherein said coupling passage is U-shaped.

10. The ventricular assist device set forth in claim 9 wherein said housing defines a pair of turbine receptacles and wherein said first and second turbine pumps each include;

a respective turbine receptacle:

a turbine rotatably supported within said turbine receptacle:

a magnetic rotor rotatable with and supported by said turbine and a drive coil supported within said housing and encircling said turbine receptacle, said turbine and said magnetic rotor.

11. The ventricular assist device set forth in claim 10 wherein said turbines each include:

a turbine shaft having bearings at opposed ends thereof; and a helical turbine blade supported upon and extending from said turbine shaft defining an outer edge.

12. The ventricular assist device set forth in claim 11 wherein each of said magnetic rotors is cylindrical and defines a respective interior surface and wherein each of said of turbine blades receives said respective interior surface to join said magnetic rotor to said turbine blade.

13. The ventricular assist device set forth in claim 8 wherein said coupling passage is V-shaped.

* * * * *